(12) United States Patent
Kelleher et al.

(10) Patent No.: US 9,795,362 B2
(45) Date of Patent: Oct. 24, 2017

(54) METHOD, SYSTEM, AND APPARATUS FOR CRANIAL ANATOMY EVALUATION

(76) Inventors: Brian Kelleher, Del Mar, CA (US); Kabir Gambhir, San Diego, CA (US)

( * ) Notice: Subject to any disclaimer, the term of this patent is extended or adjusted under 35 U.S.C. 154(b) by 957 days.

(21) Appl. No.: 14/232,570

(22) PCT Filed: Jul. 23, 2012

(86) PCT No.: PCT/US2012/000330
§ 371 (c)(1),
(2), (4) Date: Jan. 13, 2014

(87) PCT Pub. No.: WO2013/012441
PCT Pub. Date: Jan. 24, 2013

(65) Prior Publication Data
US 2014/0163385 A1    Jun. 12, 2014

Related U.S. Application Data

(60) Provisional application No. 61/510,480, filed on Jul. 21, 2011, provisional application No. 61/510,884, filed on Jul. 22, 2011.

(51) Int. Cl.
| | | |
|---|---|---|
| A61B 5/1455 | (2006.01) | |
| A61B 8/00 | (2006.01) | |
| A61B 5/00 | (2006.01) | |
| A61B 5/026 | (2006.01) | |
| A61B 5/05 | (2006.01) | |
| A61B 8/08 | (2006.01) | |
| A61B 5/107 | (2006.01) | |
| A61B 5/03 | (2006.01) | |
| A61B 5/0476 | (2006.01) | |
| A61B 8/06 | (2006.01) | |

(52) U.S. Cl.
CPC .......... *A61B 8/4416* (2013.01); *A61B 5/0004* (2013.01); *A61B 5/0059* (2013.01); *A61B 5/0075* (2013.01); *A61B 5/026* (2013.01); *A61B 5/05* (2013.01); *A61B 5/1079* (2013.01); *A61B 5/6814* (2013.01); *A61B 8/0808* (2013.01); *A61B 8/0858* (2013.01); *A61B 8/5223* (2013.01); *A61B 8/54* (2013.01); *A61B 5/031* (2013.01); *A61B 5/0476* (2013.01); *A61B 5/0507* (2013.01); *A61B 5/14553* (2013.01); *A61B 5/6803* (2013.01); *A61B 5/7257* (2013.01); *A61B 8/06* (2013.01); *A61B 8/4427* (2013.01); *A61B 8/46* (2013.01)

(58) Field of Classification Search
CPC ............................ A61B 5/0059; A61B 5/4094
See application file for complete search history.

(56) References Cited

U.S. PATENT DOCUMENTS

| | | |
|---|---|---|
| 2004/0054248 A1 | 3/2004 | Kimchy |
| 2005/0245831 A1 | 11/2005 | Banet |
| 2008/0039718 A1 | 2/2008 | Drinan |
| 2008/0154130 A1 | 6/2008 | Weiss |

(Continued)

*Primary Examiner* — Michael D Abreu
(74) *Attorney, Agent, or Firm* — Merle W Richman, Esq.

(57) ABSTRACT

Embodiments of portable cranial anatomy injury evaluation systems, apparatus, and methods are described generally herein where the system and apparatus may include multiple signal generation devices including photonic, acoustic, and electrical signals. Other embodiments may be described and claimed.

20 Claims, 13 Drawing Sheets

(56) References Cited

U.S. PATENT DOCUMENTS

| | | |
|---|---|---|
| 2009/0062660 A1* | 3/2009 | Chance ............... A61B 5/0059 600/476 |
| 2010/0041962 A1 | 2/2010 | Causevic |
| 2010/0191079 A1 | 7/2010 | Shoureshi |
| 2011/0137381 A1 | 6/2011 | Lee |
| 2011/0152249 A1 | 6/2011 | Borsook |

* cited by examiner

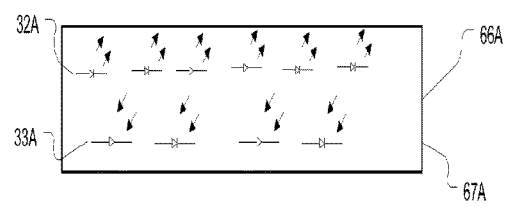
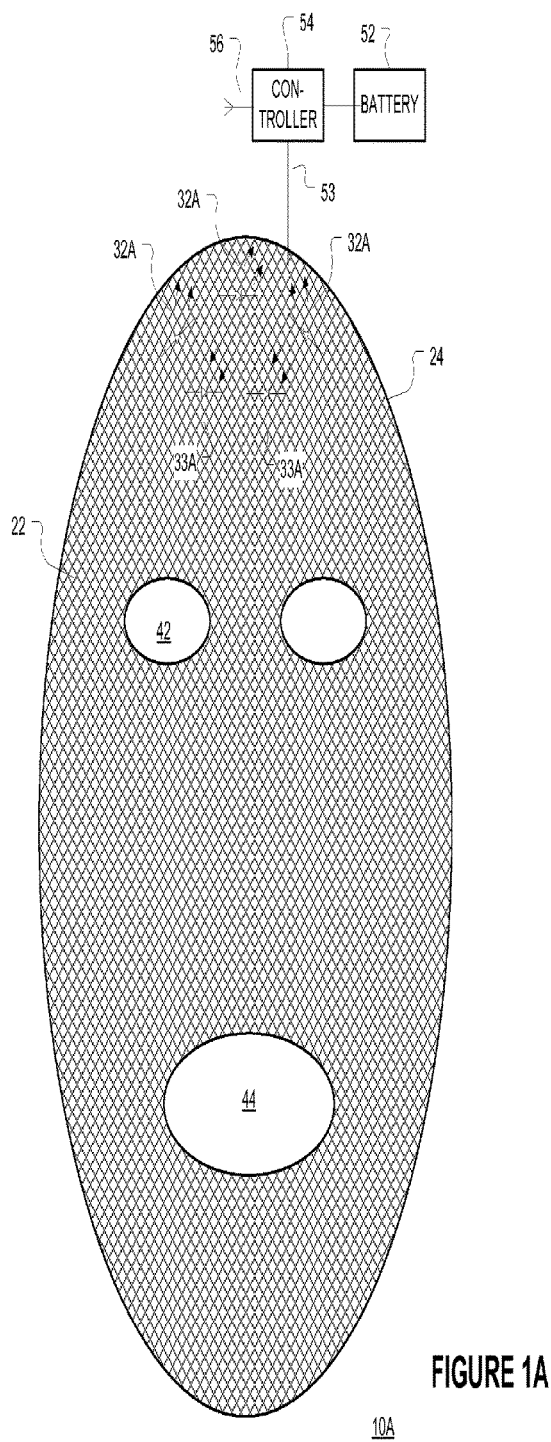
FIGURE 1A
FIGURE 2A
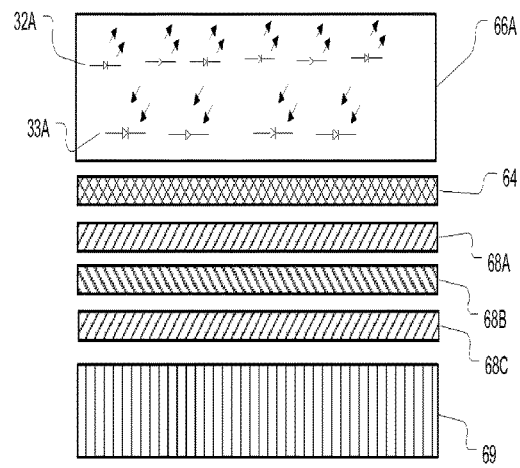
FIGURE 3A

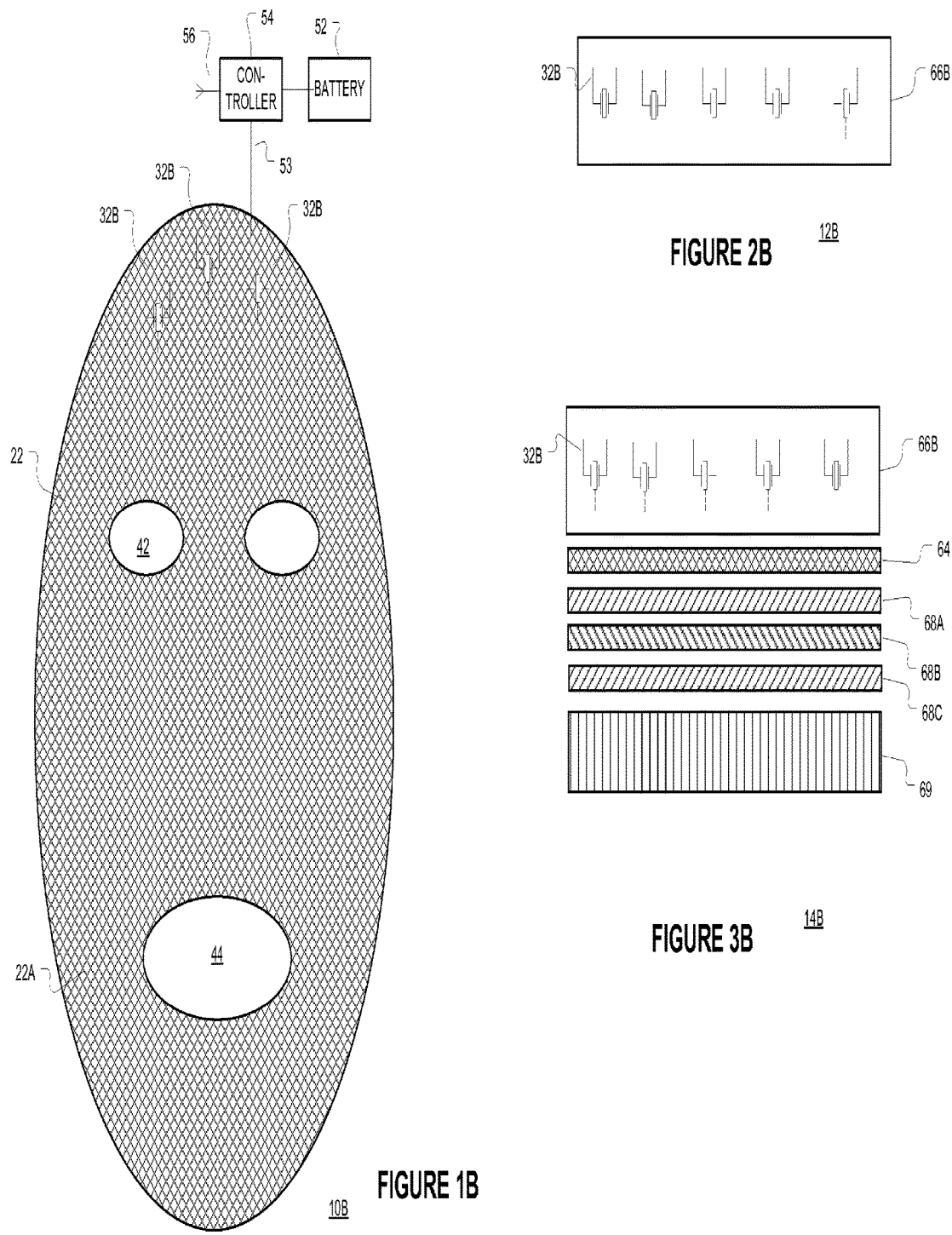

250  FIGURE 4A

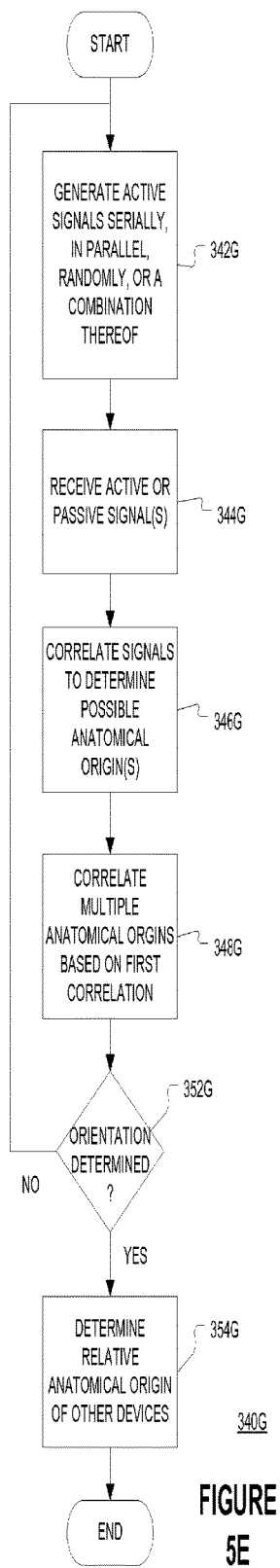
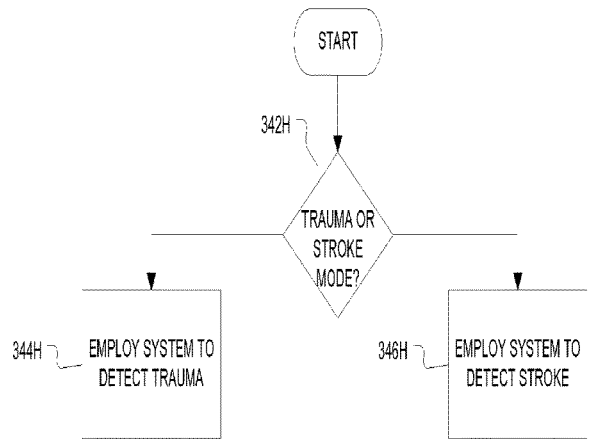
FIGURE 5E
FIGURE 5F

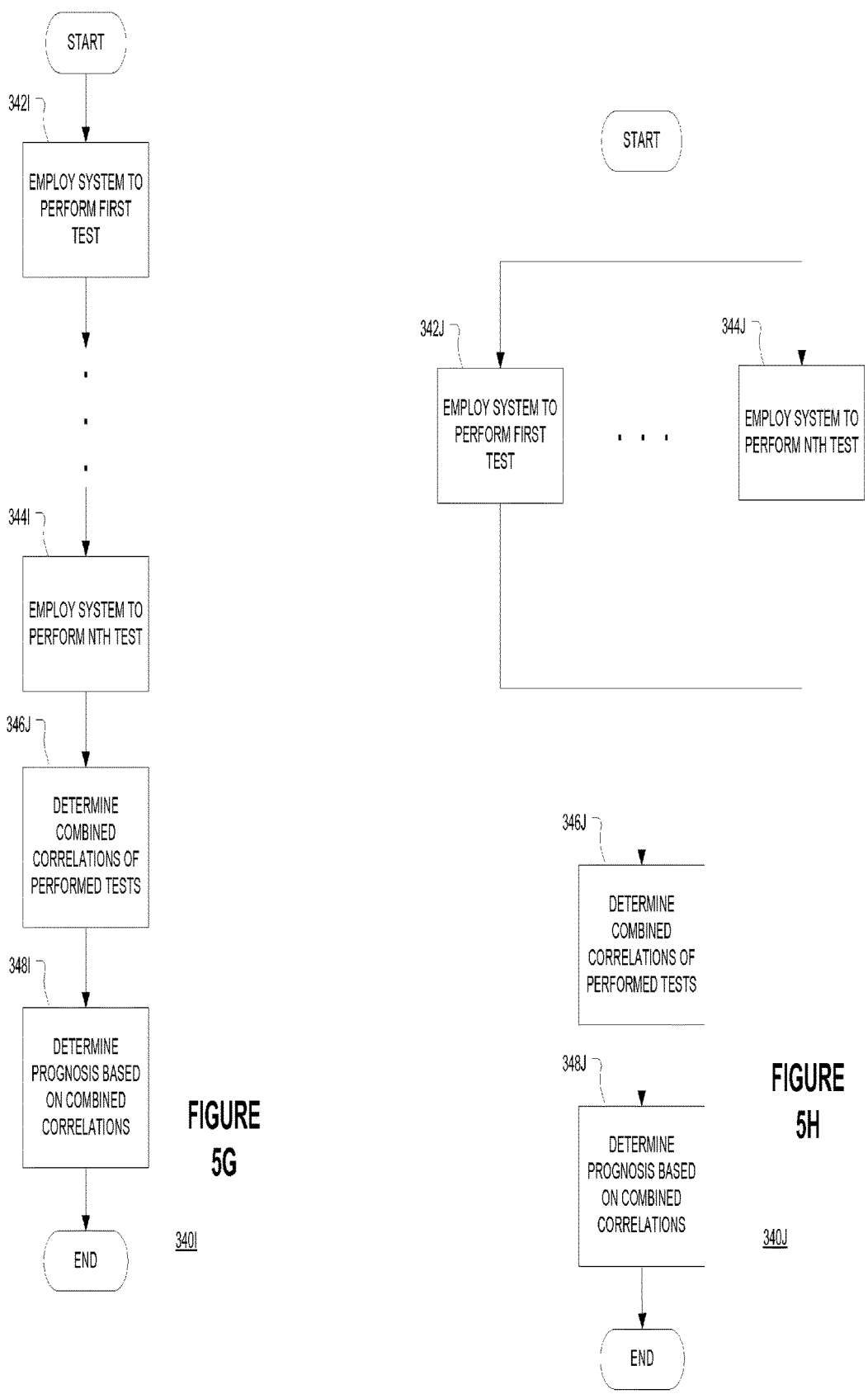

METHOD, SYSTEM, AND APPARATUS FOR CRANIAL ANATOMY EVALUATION

CROSS REFERENCE TO RELATED APPLICATIONS

The present application is related to and claims priority to U.S. Provisional Application No. 61/510,480, entitled "METHOD, SYSTEM, AND APPARATUS FOR CRANIAL ANATOMY EVALUATION", filed Jul. 21, 2011, and US Provisional Application No. 61/510,884, entitled "METHOD, SYSTEM, AND APPARATUS FOR CRANIAL ANATOMY EVALUATION", filed Jul. 22, 2011, each of which is incorporated by reference.

TECHNICAL FIELD

Various embodiments described herein relate generally to evaluating cranial anatomy including brain anatomy.

BACKGROUND INFORMATION

It may be desirable to monitor or evaluate cranial anatomy; the present invention provides a system, apparatus and method for same.

BRIEF DESCRIPTION OF THE DRAWINGS

FIGS. 1A-1E are simplified diagrams of a cranial anatomy evaluation architecture according to various embodiments.

FIGS. 2A-2E are simplified diagrams of a cranial anatomy evaluation systems according to various embodiments.

FIGS. 3A-3D are simplified cross section drawings of a cranial anatomy evaluation architecture according to various embodiments.

FIG. 4A-4C are diagrams of signals that may be applied to one or more cranial anatomy evaluation systems according to various embodiments.

FIG. 5A-5H are flow diagrams illustrating cranial anatomy evaluation processing algorithms according to various embodiments.

DETAILED DESCRIPTION

Figure 1C:
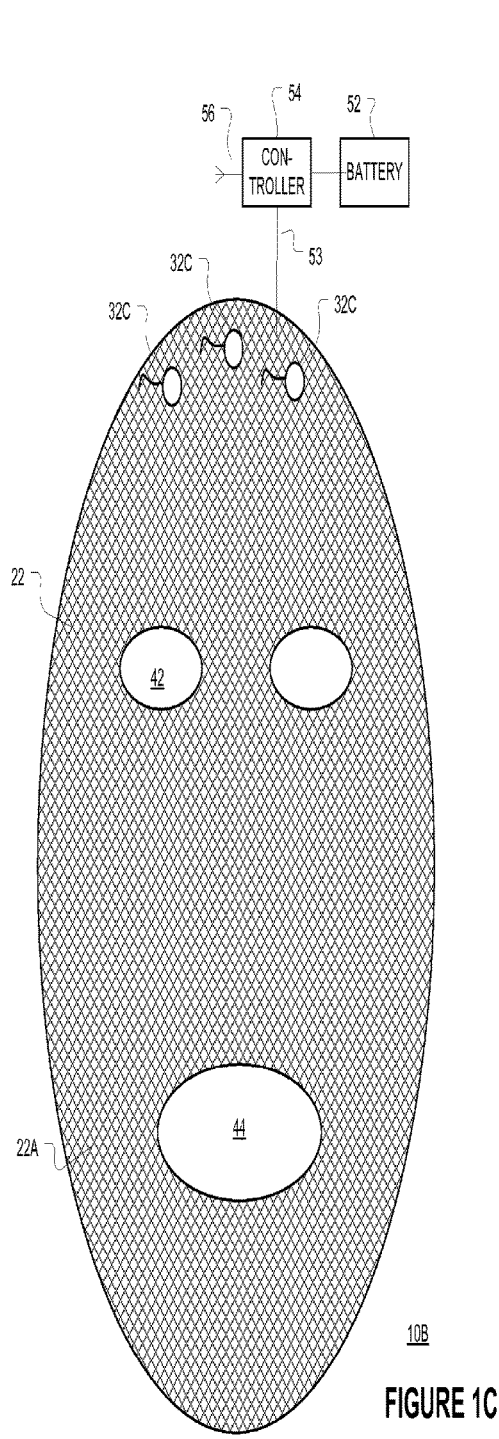
Figure 1D:
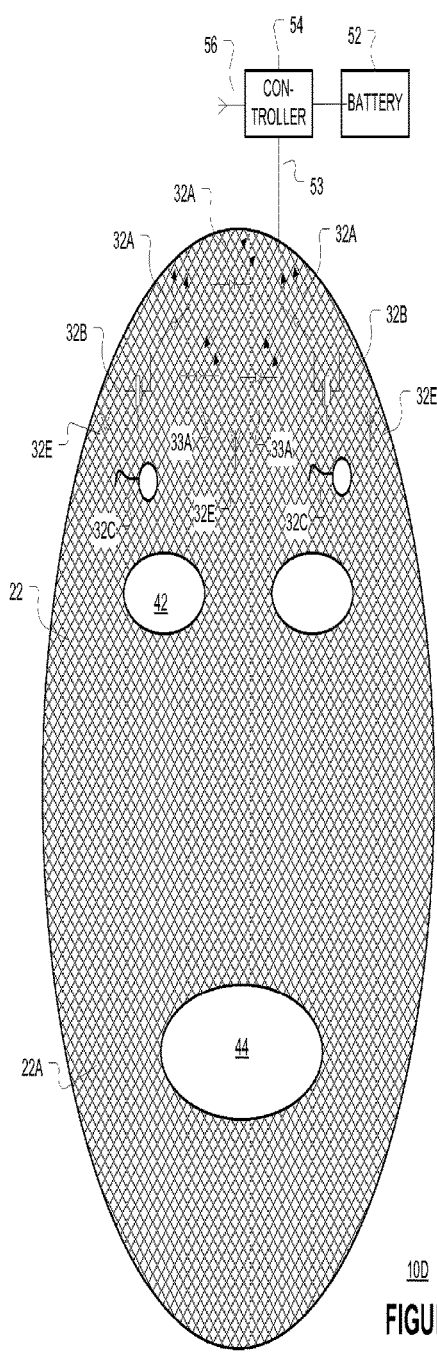
Figure 2D:
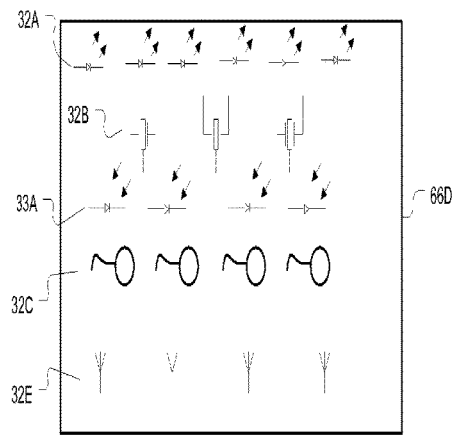
Figure 3D:
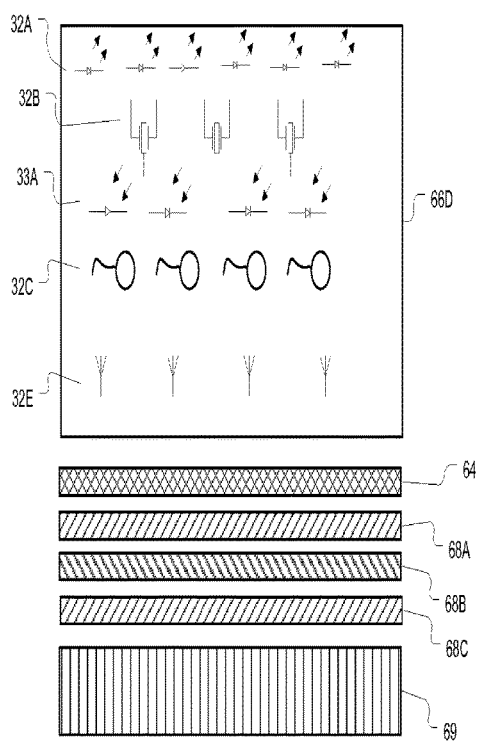

FIG. 1A is a simplified diagram of a cranial anatomy evaluation system 10A according to various embodiments. The cranial anatomy evaluation system 10 may have a planar material 67A that includes a plurality of embedded or surface photon generation modules or devices (PGD) 32A, a plurality of embedded or surface photon detection modules or devices (PDD) 33A, an electrical energy storage module or device (such as a battery or capacitor) 52, a controller 54, a coupling wire 53, and an antenna 56. The system 66A, (66B in FIG. 1B, 66C in FIG. 1C, and 66D in FIG. 1D) may include devices 32A, 33A, 32B, 32C, 32E that are to be placed around the upper cranium 24 of a patient's head 22 where the eyes 42 and mouth 44 are shown in general.

The controller 54 may generate signals to be communicated via a PGD 32A, transducer 32B (FIG. 2B), and antenna 32E (FIG. 2E) using various patterns or frequencies. The controller 54 may also receive signals from a PDD 33A, transducer 32B, electrode 32C (FIG. 1A, FIG. 1B, FIG. 1C), or antenna 32E and process the signals using various algorithms (FIGS. 5A-5J) to determine a patient cranial anatomy status or prognosis. The controller 54 may include a display (388 FIG. 6) to indicate the status or prognosis via graphs, words, audio, and numbers. The controller 54 via the antenna 56 may communicate the status or prognosis to other devices via various protocols and networks including wide area internet protocol networks, cellular networks, and satellite based networks. A controller 54 via the antenna 56 may also receive signal generation commands or instructions and patient prior recorded data for similar signals or visual/audio stimuli.

Figure 1E:
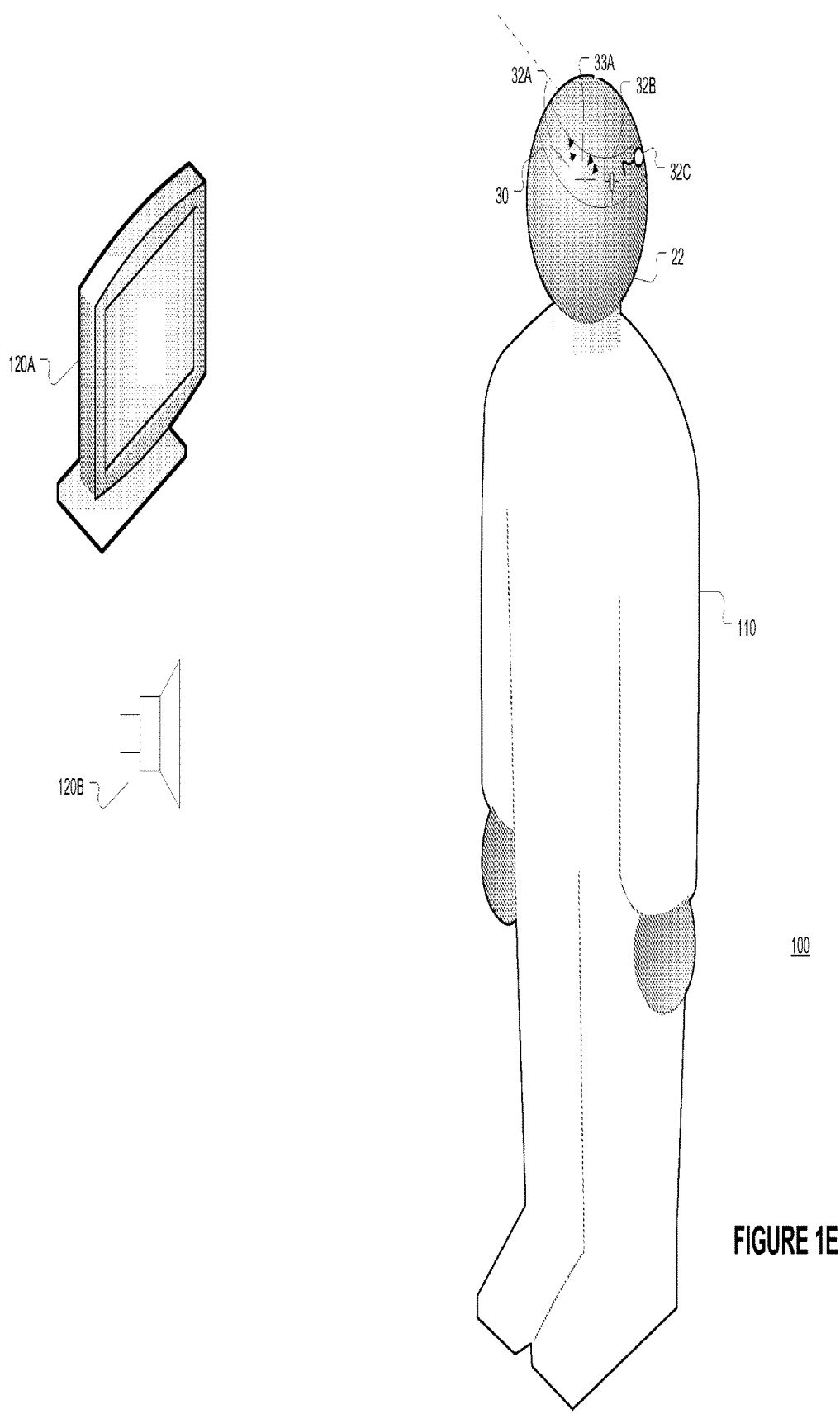

The system 66A, (66B in FIG. 1B, 66C in FIG. 1C, and 66D in FIG. 1D) planar material 67A, 67B, 67C, 67D and related devices 32A, 33A, 32B, 32C, 32E may be located around the entire cranium 24 circumference (as shown in FIG. 1E) or various sections thereof at predetermined and known locations. The planar material may include a reflective material such as a metal, pliable sheet to reflect optical signals toward the patient's cranium 24. The planar material 67A-67D may be formed of a pliable material including silicon and various polymers. In an embodiment the planar material 67A-67D may include photo transmissive sections to enable photon conductance or transmission from an embedded PGD 32A to a cranium 24 and to an embedded PDD 33A from a cranium 24.

Figure 4B:
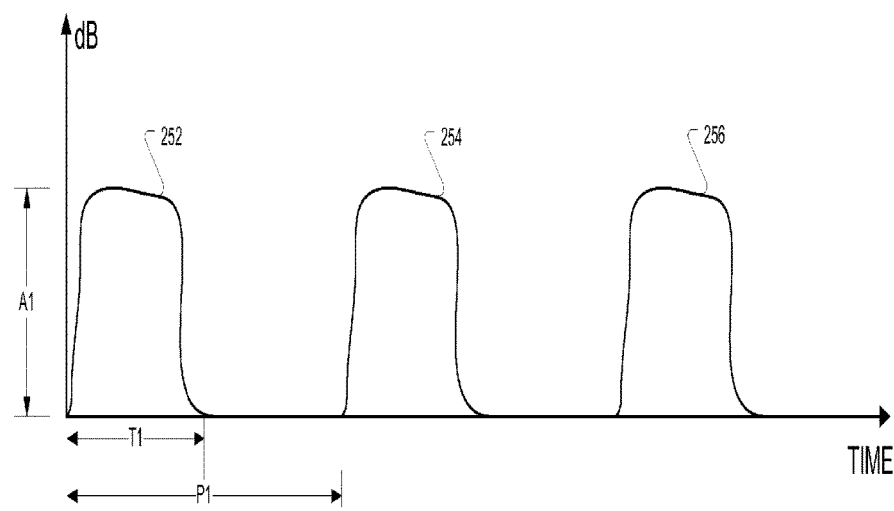
Figure 4B:
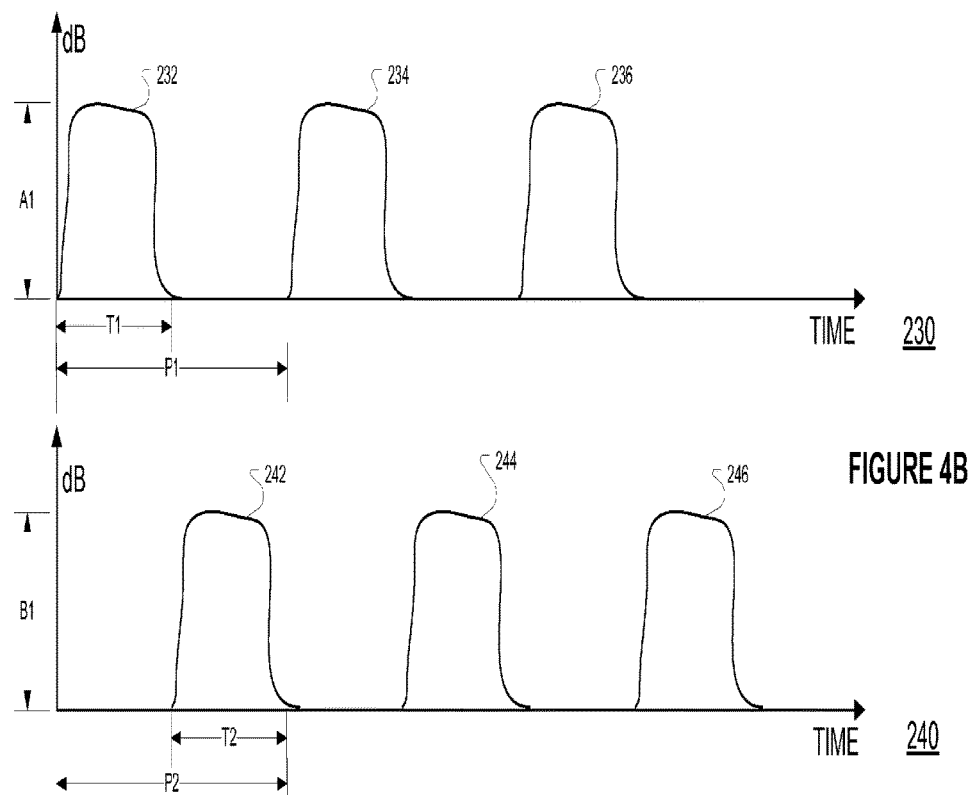
Figure 4C:
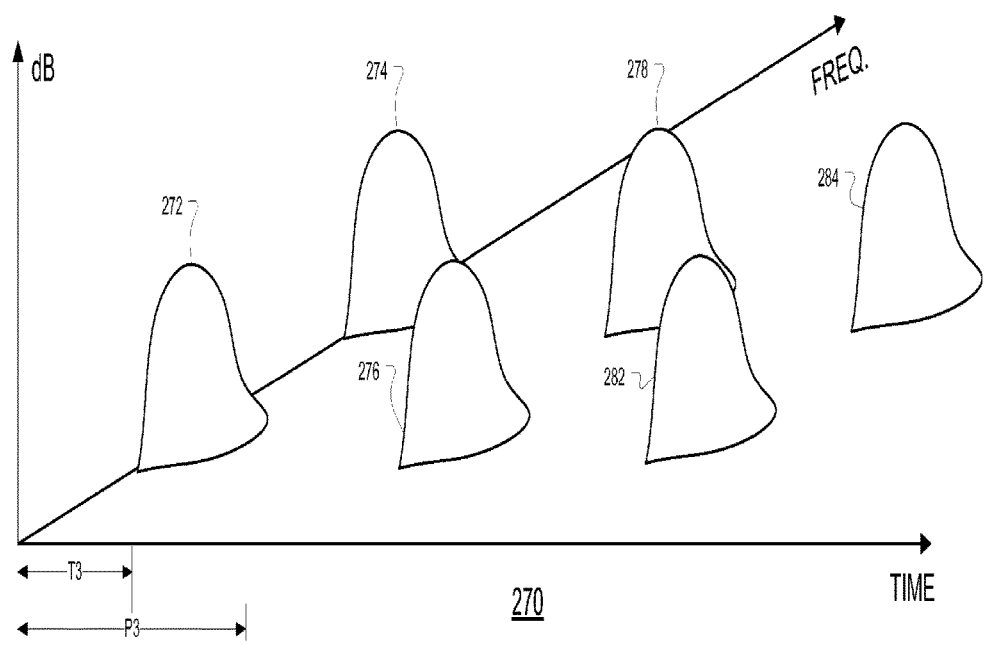

In system 66A, an embedded PGD 32A may generate photons having one or more frequencies such as the signals shown in FIGS. 4A-4C via any combination of one or more light emitting diodes (LED)s, incandescent, electroluminescent, and LASER photon generation devices. One or more PGD 32A may generate infra-red or near infra-red signals. Transmitted and received/reflected optical signals may be communicated with/within the patient's cranium 22. The received/reflected optical signals may be evaluated using digital signal processing (DSP) techniques including evaluating the frequency content of the received signals via frequency transforms including Fast Fourier Transforms (FFT). The received/reflected signals may also be correlated to stored signals for the patient or other patients having specific cranial anatomy status (injured or healthy) or various tissue states, ischemic or hemorrhagic tissue.

Figure 2C:
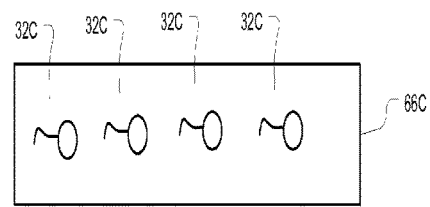
Figure 2E:
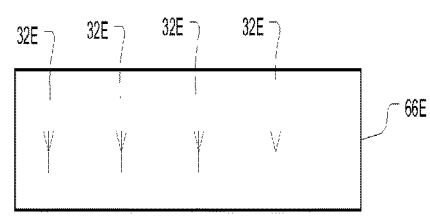
Figure 3C:
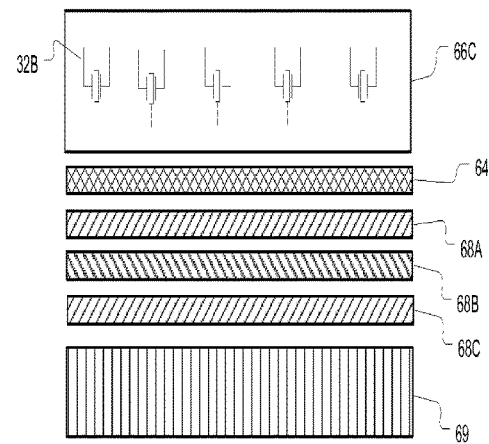

A cranial anatomy evaluation apparatus 66A is shown in FIG. 2A. The apparatus 66A includes the planar material 67A, PGD 32A, and PDD 33A. The planar material 67A may include flexible material so the apparatus 66A may conform to the cranium of a patient 22. The apparatus 66A or system 10A may be compact and portable for use in the field. FIG. 3A is a simplified cross sectional diagram of an apparatus 66A applied to a patient's cranium. As shown in FIG. 3A a patient's cranium 24 may include cranium bone 64, a dura mater layer 68A, an arachnoid layer 68B, a pia mater layer 68C, and brain tissue 69. Cerebrospinal fluid may flow between the arachnoid layer 68B and the pia mater 68C.

When subject to trauma, a patient's cranial anatomy 24 may be damaged, producing focal and diffuse hemorrhaging and ischemia. Hemorrhaging may occur in the different layers 68A, 68B, 68C, between the layers and within the brain tissue 69 and brain ventricles. Such bleeding is called an epidural hematoma when bleeding exists between the dura mater 68A and the cranial bone 64, a subdural hematoma when bleeding exists between the dura mater 68A and the arachnoid layer 68B, and a subarachnoid hemorrhage when bleeding existing between the arachnoid mater 68B and pia mater 68C.

Hemorrhaging within the confined cranial space may increase the effective intracranial pressure (ICP). Increased ICP can lead to brain tissue 69 rupture or ischemia (lack of oxygen to brain tissue 69) and ultimately to brain tissue death or stroke. It may be critical to diagnosis cranial anatomy injury in the field at or near the time of injury (such as blunt force or penetrating force trauma) to prevent or limit brain tissue damage due to secondary events including lack of oxygen or ischemia and brain tissue rupture due to internal bony protrusion(s) compressed against brain tissue 69 due to elevated ICP.

In order to accurately and effectively detect cranial trauma including focal and diffuse hemorrhaging and ischemia, different signal modalities (energy types) may be employed and evaluated serially or in combination to predict potential injury. Further a patient or general patient pre-trauma response to the signal modalities and various video and audio signal stimuli (FIG. 1E) may be recorded and used a base line for determining whether potential injuries have occurred. As shown in FIGS. 1B-3B one or more acoustic transducers 32B may be employed to generate and receive acoustic signals communicated into a patient's cranium 24. The acoustic transducers 32B generate and receive ultrasonic energy and Doppler processing may be performed to evaluate the received signal(s). In an embodiment a transducer 32B may be deployed by or located near a transtemporal window to enable evaluation of a patient's 22 middle cerebral artery, internal carotid artery bifurcation, anterior cerebral artery, and posterior cerebral artery. The transtemporal window lies within the area of the zygomatic arch.

Further a transducer 32B may be deployed by or located near a transorbital window to enable insonation of a patient's 22 ophthalmic artery and internal carotid artery siphon. A transducer 32B may be deployed by or located near a sub-occipital window to enable serial evaluation of major portions of a patient's 22 vertebral and basilar arteries. The controller 54 may employ a DSP to evaluate the frequency content of a received transducer signal. In an embodiment the controller 54 may use a DSP to determine the FFT (Fast Fourier Transform) of received signals. The resultant, transformed signals may be used to determine mean blood flow velocity, pulsatility index, and other diagnostic parameters.

As shown in FIGS. 1D, 2D, 2E, and 3D one or more electrical antennas 32E may be employed to generate and receive electrical signals communicated into a patient's cranium 24. The electrical antennas 32E may generate and receive various frequency electrical energy and signal processing may be performed to evaluate the received signal(s). In an embodiment an antenna 32E may be deployed by or located near a transtemporal window to enable evaluation of a patient's 22 middle cerebral artery, internal carotid artery bifurcation, anterior cerebral artery, and posterior cerebral artery.

Further an antenna 32E may be deployed by or located near a transorbital window to enable radiation of a patient's 22 ophthalmic artery and internal carotid artery siphon. An antenna 32E may be deployed by or located near a sub-occipital window to enable serial evaluation of major portions of a patient's 22 vertebral and basilar arteries. The controller 54 may employ DSP to evaluate the frequency content of a received antenna signal. In an embodiment the controller 54 may use DSP to determine the FFT (Fast Fourier Transform) of received signals. The resultant, transformed signals may be used to determine mean blood flow velocity, pulsatility index, and other diagnostic parameters. In an embodiment the controller 54 may use a combination of multiple signals from different signal generation devices including a PDD 33A, transducer 32B, electrode 32C, and antenna 32E to determine or evaluate the state of one or more attributes of a patient's cranial anatomy. It is noted that an antenna 32E may generate signals having various frequency content including signals with radio frequency content. The frequency content may be selected based on the anatomy or tissue about the antenna 32E and the condition (s) to be evaluated.

The controller 54 may correlate each of the signals to prior patient, general patient, or related signal content. The prior patient, general patient, or related signal content may be stored in memory (such as RAM 384, ROM 406 shown in FIG. 6) and include signals representing anatomy with and without physical attributes including healthy, ischemic, and hemorrhagic tissue. The stored signal content may vary based on the anatomy, physical tissue state, and type of received signal (electrical, photonic, and acoustic). In an embodiment, the controller 54 may correlate received signal data from a device 33A, 32B, 32C, 32E to healthy tissue, and other tissue states and determine the tissue status based on the correlation. In an embodiment the controller 54 may use the algorithm 340G shown in FIG. 5E to orient one or more devices 32A, 33A, 32B, 32C, 32E with a patient anatomy. The controller 54 may then select stored signals based on the anatomy at or near the signal producing device 33A, 32B, 32C, 32E. It is noted that the controller 54 may also store received signal data from devices 33A, 32B, 32C, 32E (after converting to digital data in an embodiment) and compare subsequent signal data to determine if the state of suspect tissue has changed, e.g., after a traumatic event monitoring dura mater layer 86A tissue to detect possible bleeding and increasing ICP.

As shown in FIGS. 1C-3C one or more electrodes 32C may be employed to passively receive electrical signals generated by a patient's cranium 24 to generate an electroencephalogram (EEG). The electrodes 32C may receive the electrical signals and DSP algorithms may be used to evaluate the received signal(s) including FFT (evaluation of the frequency content of the signal) to generate or produce an EEG or other diagnostic signals. As shown in FIGS. 1D-3D a cranial anatomy evaluation system 66D may employ one or more electrodes 32C, one or more PGD 32A, one or more PDD 33A, one or more antennas 32E, and one or more acoustic transducers 32B. In this system 10D acoustic, electrical, and photonic signals may be generated (simultaneously or serially) and the resultant signals (photonic, acoustic, and electrical) may be received by a PDD 32A, transducer 32B, antennas 32E, and electrode 32C. The combined systems may be simultaneously evaluated to more effectively predict or determine cranial anatomy injury (CAI) including trauma and strokes.

FIG. 1E is a diagram of a CAI evaluation architecture 100 according to various embodiments. In architecture 100 a flexible band or cap 30 may include one or more signal generation or receiving devices 32A, 33A, 32B, 32C, 32E. The flexible band or cap 30 may include anatomical markers such as eye or ear locations to enable a consistent placement of the various devices 32A, 33A, 32B, 32C, 32E relative to cranial anatomy. In an embodiment the flexible band 30 may include a plurality of signal generation or receiving devices 32A, 33A, 32B, 32C, 32E at known locations in the band or cap 30 including radial location. A system 10A, 10B, 10E, 100 controller 54 may employ the algorithm 340G shown in FIG. 5E to determine or register the anatomical location of one or more of the plurality of signal generation or receiving devices 32A, 33A, 32B, 32C, 32E.

As shown in FIG. 5E, the algorithm 340G may employ one or more devices 32A, 32B, 32E to actively generate signals (activity 342G). As noted the devices 32A, 32B, 32E may have known physical locations in the system 10A, 10B, 10E, 100 including radially, axially, and vertically. A controller 54 may generate signals having characteristics to resonate or respond to a particular anatomy or tissue. The various signal characteristics and shapes may be stored in the ROM 406 or RAM 384 (FIG. 6). A controller 54 may use particular signals with particular devices 32A, 32B, 32E to determine if the particular device is at or about particular anatomy. The controller 54 may use a similar signal for similar devices in the system 10, 10A, 10B, 100 to isolate a particular anatomy. The isolation of a particular anatomy may enable the controller 54 to determine the location of one or more devices 32A, 32B, 32C, 32E relative a patient's anatomy (activity 348G). The controller 54 may then be able to determine the physical location of other devices 32A, 32B, 32C, 32E based on the other determination (activity 354G). When a particular signal does not yield a high correlation with an expected signal for a particular anatomy (activity 352G), the controller 54 use one or more additional signals or look for one or more different responses to correlate the location of a device 32A, 32B, 32C, 32E to a patient's anatomy. In an embodiment the controller may not employ activity 342G and receive signals from the devices 32C, 32E passively.

In an embodiment, the controller 54 via the algorithm 340G may use signals to determine a device 32A, 32B, 32C, 32E is located near a transtemporal window by evaluating a patient's 22 middle cerebral artery, internal carotid artery bifurcation, anterior cerebral artery, and posterior cerebral artery. Further the controller 54 via the algorithm 340G may use signals to determine a device 32A, 32B, 32C, 32E is located near a transorbital window by evaluating a patient's 22 ophthalmic artery and internal carotid artery siphon.

In architecture 100 additional stimuli such as video signals generated by a monitor 120A or hearable acoustic signals (audio signals) generated by a speaker 120B may generate random or predetermined patterns or sounds that may aid in the assessment of CAI. CAI evaluation architecture 100 may be employed to evaluate a patient when healthy. The resultant signals may be stored and then compared or correlated with future patient signals to determine CAI status. It is noted that the systems 66A to 66D and 30 may be larger, rigid constructs that are placed on top or about a patient's head 22.

FIGS. 4A-4B are diagrams of signal waveforms 230, 240, 250 that may be applied to one or more signal generators PGD 32A, transducers 32B, or antennas 32E according to various embodiments. The signal waveform 250 includes several square-wave pulses 252, 254, 256 that may be applied to a signal generator 32A, 32B, 32E where each pulse 252, 254, 256 may a have a similar magnitude and envelope. A waveform 250 may be used to energize a signal generator 32A, 32B, 32E periodically P1 for a predetermined interval T1 where each pulse 252, 254, 256 has a amplitude A1. In an embodiment, A1 may be about 0.1 milliamperes (mA) to 10 mA, the pulse width T1 may be about 100 microsecond (μs) to 500 μs and the period P1 may from 100 ms to 500 ms as a function of the energy required to pass into a patient's cranium 24. In another embodiment, A1 may be about 0.5 milliamperes (mA) to 5 mA, the pulse width T1 may be about 200 microsecond (μs) and the period P1 may about 250 ms as a function of the energy required to pass into a patient's cranium 24.

In FIG. 4B a signal waveform 230 may be applied to a first signal generator 32A, 32B, 32E module or group and a second waveform 240 may be applied or used to energize a second signal generator 32A, 32B, 32E module. The signal waveform 230 includes several square-wave pulses 232, 234, and 236 and the signal waveform 240 includes several square-wave pulses 242, 244, and 246 where each pulse 232, 234, 236, 242, 244, 246 may a have a similar magnitude and envelope. The waveform 230 may be used to energize a first PGD 32A, 32B, 33, 332, transducer 32B, or antenna 32E module periodically P1 for a predetermined interval T1 where each pulse 232, 234, 236 has an amplitude A1. The waveform 240 may be used to energize a second first PGD 32A, 32B, 33, 332, transducer 32B, or antenna 32E module periodically P2 for a predetermined interval T2 where each pulse 242, 244, 246 has an amplitude B1. The pulse width T1, T2 may be about 100 microsecond (μs) to 500 μs and the period P1, P2 may from 100 ms to 500 ms as a function of the energy required to pass into a patient's cranium 24. In another embodiment, A1, A2 may be about 0.5 milliamperes (mA) to 5 mA, the pulse width T1, T2 may be about 200 microsecond (μs) and the period P1, P2 may about 250 ms as a function of the energy required to pass into cranium anatomy. In an embodiment the pulses 232, 234, 236 do not substantially overlap the pulses 242, 244, 246. In an embodiment T1>T2 and P2 is an integer multiple of P1.

FIG. 4C depicts a waveform 270 that includes multiple pulses 272, 274, 276, 278, 282, and 284 that may not overlap in the time or the frequency domain. In an embodiment each pulse 272, 274, 276, 278, 282, and 284 may have a pulse width T3, and frequency spectrum width F1 and period P3. The pulse 272 is frequency offset from the pulse 274, the pulse 276 is frequency offset from the pulse 278, and the pulse 282 is frequency offset from the pulse 284. The pulses 272, 274, 276, 278, 282, and 284 may be applied to a PGD 32A, 32B, 33, 332, transducer 32B, or antenna 32E module to affect cranium anatomy. Pulses 272, 274 having different frequency spectrums may enable different PGD 32A, 32B, 33, 332, transducer 32B, or antenna 32E module stimulation. In an embodiment the pulses 272, 276, 282 may be applied to a first PGD 32A, 32B, 33, 332, transducer 32B, or antenna 32E module and the pulses 274, 278, 284 may be applied to a second PGD 32A, 32B, 33, 332, transducer 32B, or antenna 32E module. The frequency separation between the respective pulses may enable simultaneous energization of a first, second, and third PGD 32A, 32B, 33, 332, transducer 32B, or antenna 32E module and subsequent and independent spectrum generation.

Figure 5A:
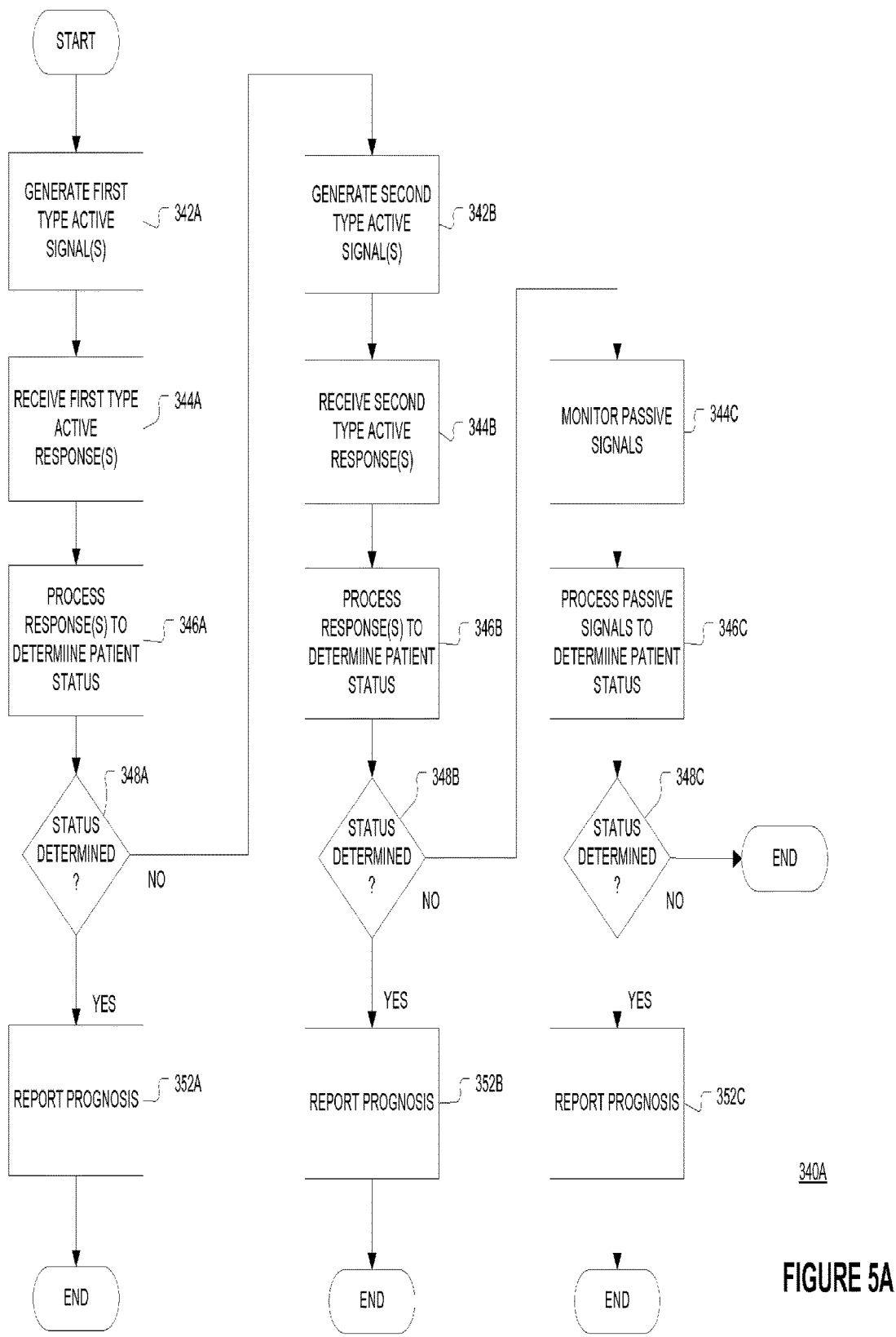

In an embodiment the invention may employ the algorithms 340A, 340D to 340J as shown in FIGS. 5A to 5H to evaluate CAI or cranium status. A CAI evaluation serial method 340A is shown in FIG. 5A. In the method 340A, a system 10, 10A, 10B, 100 may generate a first type active signal via a device 32A, 32B, 32C, 32E towards a patient's cranium 24 (activity 342A). A device 33A, 32B, 32C, 32E may receive the first type active response signals reflected from the patients cranial anatomy (activity 344A). The method 340A may then process the received response signals using various signal processing algorithms including FFTs to determine a patient's cranium anatomy status (activity 346A) including accounting for the device 32A, 32B, 32C, 32E location relative to the patient's cranial anatomy. When the resultant status is considered conclusive or within acceptable standard(s) (activity 348A), the CAI status or prognosis may be reported (activity 352A). When the status is not conclusive another evaluation signal or technique may be employed. It is noted that the order of signal employment/evaluation, and device 32A, 32B, 32C, 32E deployment may not be critical and may be processed in any order in the method 340A.

In the method 340A, a second type device 32A, 32B, 32C, 32E may be employed to generate second type active signals towards a patient's cranium 24 (activity 342B). The second type device 32A, 32B, 32C, 32E or device 33A may receive second type active response signals reflected from the patient's cranial anatomy (activity 344B). The method 340A may then process the received second type response signals using various signal processing algorithms including FFTs to determine a patient's cranium anatomy status (activity 346B) including accounting for the second type device 32A, 32B, 32C, 32E location relative to the patient's cranial anatomy. When the resultant status is considered conclusive or within acceptable standard(s) (activity 348B), the CAI status or prognosis may be reported (activity 352B). When the status is not conclusive another evaluation signal or technique may be employed.

Similarly, in the method 340A a device 32A, 32B, 32C, 32E may receive passive signals communicated from the patient's cranial anatomy (activity 344C). The method 340A may then process the received electrical signals using various signal processing algorithms including FFTs to determine a patient's cranium anatomy status (activity 346C) including accounting for the receiving device's 32A, 32B, 32C, 32E location relative to the patient's cranial anatomy. When the resultant status is considered conclusive or within acceptable standard(s) (activity 348C), the CAI status or prognosis may be reported (activity 352C).

Figures 5B, 5C:
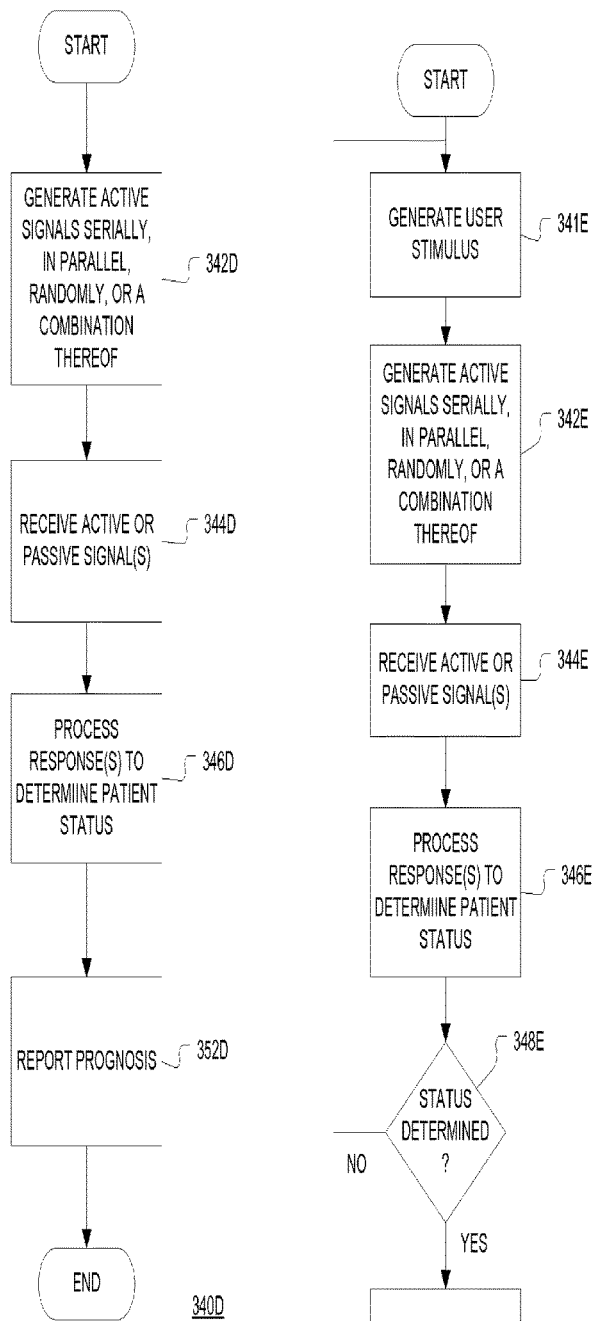
Figure 6:
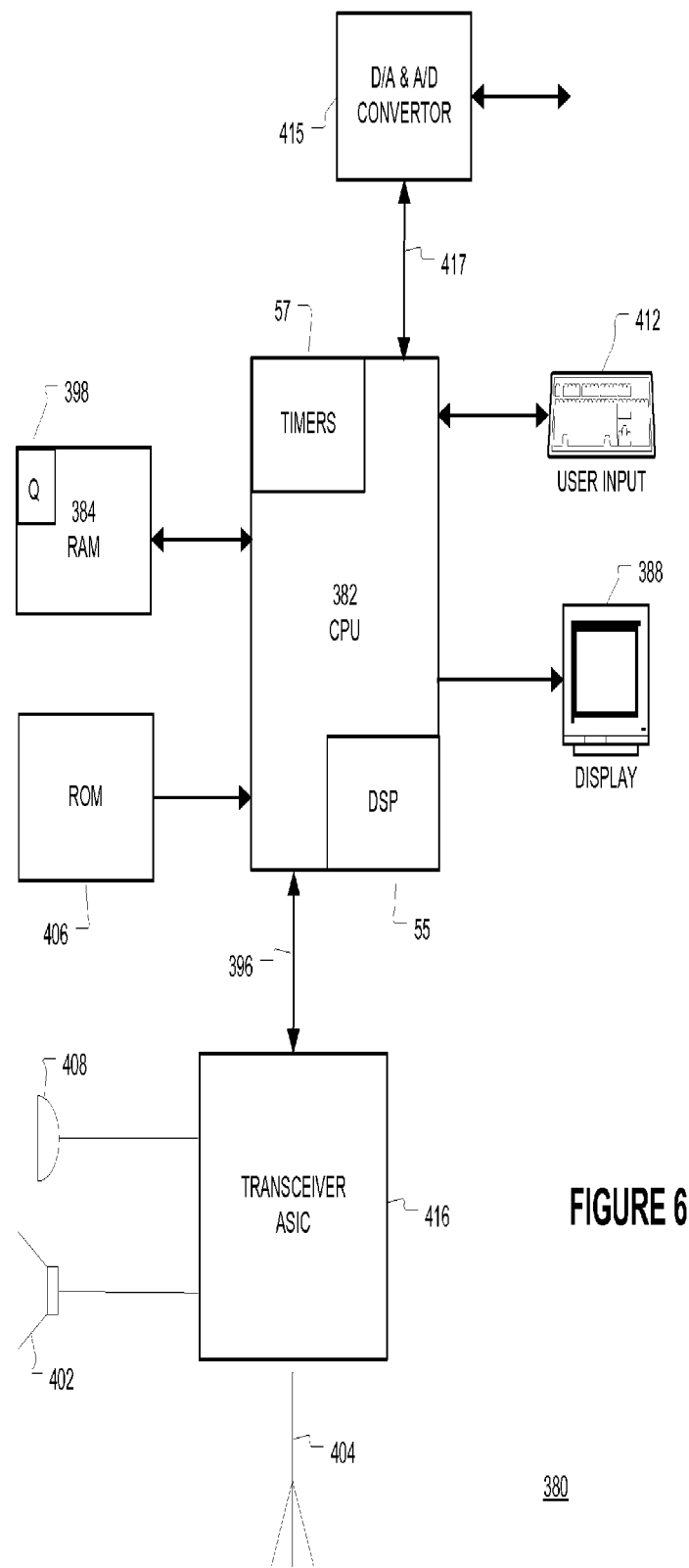
FIG. 6 is a block diagram of an article according to various embodiments.

In another method 340D shown in FIG. 5B a combination of various signals may be generated to determined CM status. In the method 340D shown in FIG. 5B, a combination of devices 32A, 32B, 32C, 32E may be employed to generate optical, electrical, and acoustic signals towards a patient's cranium 24 (activity 342D) serially, in parallel or random order. A device 33A, 32B, 32C, 32E near the transmitting devices 32A, 32B, 32C, 32E may receive acoustic, electrical, or ultrasound signals reflected from the patient's cranial anatomy, e.g., a PDD 33A at or near the PGD 32A may receive optical signals and an electrode 32C may receive electrical signals communicated from the patient's cranium 24 (activity 344D). The method 340D may then process the received acoustic signals using various signal processing algorithms including FFTs to determine a patient's cranium anatomy status (activity 346D) including accounting for the transmitting and receiving devices locations relative to the patient's cranial anatomy. The determined CAI status or prognosis may be reported (activity 352D).

In an embodiment the algorithm 340I, 340J shown in FIG. 5G, 5H may be employed by the controller 54 to evaluate a patient's cranial anatomy to determine whether the patient has suffered a traumatic event to their cranium and experienced or is experiencing a stroke including a hemorrhagic or ischemic stroke, their prognosis, and possible treatments options based on their determined state or prognosis. For example, the algorithm 340I may enable a user to determine whether a medical protocol is advisable, such as delivery of a tissue plasminogen activator (tPA). Administration of tPA after or during a stroke normally requires a computed tomography (CT) scan or magnetic resonance imaging (MRI) to confirm its safe administration. These tests (CT or MRI) may require 30 or more minutes to complete and be interpreted once the patient is scanned (processed through queues to use the respective equipment, CT or MRI). The present invention may enable a physician to determine in a more timely manner whether administration of a tPA or other treatments are possible or within acceptable protocols.

In the algorithm 340I of FIG. 5G a system 10, 10A, 10B, 100 may be employed to perform a plurality of tests (N) in a serial order (activities 342I, 344I). In the algorithm 340J of FIG. 5H a system 10, 10A, 10B, 100 may be employed to perform a plurality of tests (N) in a parallel or nearly contemporaneous order (activities 342J, 344J). In another embodiment some tests 342I, 344I, 342J, 344J may be performed serially while others are performed in parallel. A test 342I, 344I, 342J, 344J may employ one or more devices 32A, 32B, 32C, 32E to generate one or more signals and devices 33A, 32B, 32C, 32E to receive active or passive signals. Tests 342I, 344I may be performed serially where similar type of signals or devices 33A, 32B, 32C, 32E may generate or receive signals that interfere with the respective tests, e.g., tests that generate photonic energy at or near the same location. Tests 342J, 344J may be performed contemporaneously where different type of signals or devices 33A, 32B, 32C, 32E generate or receive signals that do not interfere with the respective tests, e.g., tests that generate photonic energy at or near one location and acoustic energy at or near the same or different location. In an embodiment devices 32A, 32B may be employed at or near the same location to create a combined effect on anatomy to analyzed, e.g., transmitting photonic and acoustic energy contemporaneously may have a synergic effect and enable a system 10, 10A, 10B, 100 to more accurate determine the state of cranial anatomy.

In either algorithm 340I, 304J, after or during tests 342I, 344I, 342J, 344J, the received data may be correlated with stored data representing tissue or anatomy in various states to determine prognosis or status of tissue or anatomy at or near the receiving devices 33A, 32B, 32C, 32E (activities 346J, 346I, 348I, 348J). In an embodiment received data from multiple tests 342I, 344I, 342J, 344J may be correlated with stored data representing tissue or anatomy in various states to determine prognosis or status of tissue or anatomy at or near the receiving devices 33A, 32B, 32C, 32E for the same multiple tests performed either serially or in parallel (activities 346J, 346I, 348I, 348J). The combined correlation for multiple tests may enable more accurate tissue or anatomy prognosis or status determination versus single tests. It is noted that each test performed by the system may be designed or configured to determine the status or prognosis of cranial anatomy.

In an embodiment a system 10, 10A, 10B, 100B may be employed to detect a potential midline shift in a patient's cranial anatomy (activity 342I, 344I, 342J, 344J). A controller 54 may transmit and receive near infrared signals via devices 32A, 33A to determine the presence and status of a potential hemorrhage in this test. In other test 342I, 344I, 342J, 344J, controller 54 may employ a device 32A, 32B, 32C, 32E to determine a patient's inter-cranial pressure (ICP) via an ocular location or placement of device(s), This test may be performed contemporaneously or serially with the midline shift test. A patient's ICP level may indicate whether a patient has or is suffering cranial trauma or a stroke and the magnitude of tissue damage or potential damage due to ICP level (activity 342I, 344I, 342J, 344J).

The system 10, 10A, 10B, 100 may also be employed to determine hemodynamic oxygen levels in a patient's cranial anatomy (activity 342I, 344I, 342J, 344J). A controller 54 may transmit and receive near infrared signals via devices 32A, 33A to determine hemodynamic oxygen levels in a patient's cranial anatomy and the presence and status of a potential hemorrhage (346J, 346I, 348I, 348J). A system 10, 10A, 10B, 100 may be employed to detect indirect blood flow in multiple locations in a patient's cranial anatomy (activity 342I, 344I, 342J, 344J). A controller 54 may transmit and receive near acoustic signals via devices 32B to determine indirect blood flow levels in multiple locations in a patient's cranial anatomy and the presence and status of a potential hemorrhage (activity 346J, 346I, 348I, 348J).

A system 10, 10A, 10B, 100 may be employed to detect blood flow in multiple locations in a patient's cranial anatomy (activity 342I, 344I, 342J, 344J) after a contrast dye or microbubbles have been inserted into a patient's bloodstream. A controller 54 may transmit and receive near acoustic signals via devices 32B to determine blood flow levels in multiple locations in a patient's cranial anatomy and the presence and status of a potential hemorrhage (activity 346J, 346I, 348I, 348J) where the flow detection may be enhanced by the contrast dye or microbubbles. In an embodiment a system 10, 10A, 10B, 100 may employ one or more antennas 32E to generate electrical energy in the microwave bandwidth (activity 342I, 344I, 342J, 344J).

It is noted that tissue malignancies, blood supply, hypoxia, acute ischemia, and chronic infarction may change dielectric properties of the tissue radiated by low level microwave energy. The system 10, 10A, 10B, 100 may employ one or more antennas 32E to generate low levels microwave frequency, electromagnetic energy. As noted a stroke is a disturbance in the blood supply to the brain caused by either a blocked (ischemic stroke) or burst blood vessel (hemorrhagic stroke). Analysis of received scattered low energy microwave signals at antennas 32E may enable identification of the stroke type (ischemic or hemorrhagic) and severity. Such analysis may aid in treatment protocol selections (activities 346J, 346I, 348I, 348J).

In another embodiment a system 10, 10A, 10B, 100 may be employed to detect blood flow in multiple locations in a patient's cranial anatomy (activity 342I, 344I, 342J, 344J) and compare the blood flow or frequency in another body system including their heart or lung. A controller 54 may transmit and receive near acoustic signals via devices 32B to determine blood flow levels in multiple locations in a patient's cranial anatomy (activity 346J, 346I, 348I, 348J). A separate system or addition to the system 10, 10A, 10B, 100 may enable contemporaneous determination of blood flow in another body system including heart or lungs. Comparison of the determined blood flow rates or frequencies of the cranium and other system may provide an indication of stroke type and severity (activity 342I, 344I, 342J, 344J).

Any of the above described tests may be employed by the system 10, 10A, 10B, 100 or algorithms 340A, 340D to 340J as shown in FIGS. 5A to 5H. In another method 340E shown in FIG. 5C a combination of various signals including video and audio signals may be employed to aid in determination of CAI status. In the method 340E shown in FIG. 5C, random or know video or audio signals may be directed to the patient to invoke or activity various brain activity (activity 341E). In addition, a device 32A, 32B, 32C, 32E may be employed to generate signals towards a patient's cranium 24 (activity 342E) per any of the algorithms 340A, 340D to 340J as shown in FIGS. 5A to 5H. A transducer 32B or other transducer 32B near the transmitting transducer 32B may receive acoustic or ultrasound signals reflected from the patient's cranial anatomy, a PDD 33A at or near the PGD 32A may receive optical signals, an electrode 32C may receive electrical signals communicated from the patient's cranium 24, an antenna 32E may generate and receive electrical signals or any combination thereof (activity 344E). The method 340E may then process the received acoustic signals using various signal processing algorithms including FFTs to determine a patient's cranium anatomy status (activity 346E) including accounting for the devices 32A, 32B, 32C, 33A, 32E locations relative to the patient's cranial anatomy. A system 10A, 10B, 10, 100 may employ the method 340F shown in FIG. 5D to account for the additional video/audio (V/A) signals. When CM status is determined (according to various standards) (activity 348E), the determined CAI status or prognosis may be reported (activity 352E). Otherwise the V/A signal may be changed and the method 340E repeated (activity 348E, 341E).

Figure 5D:
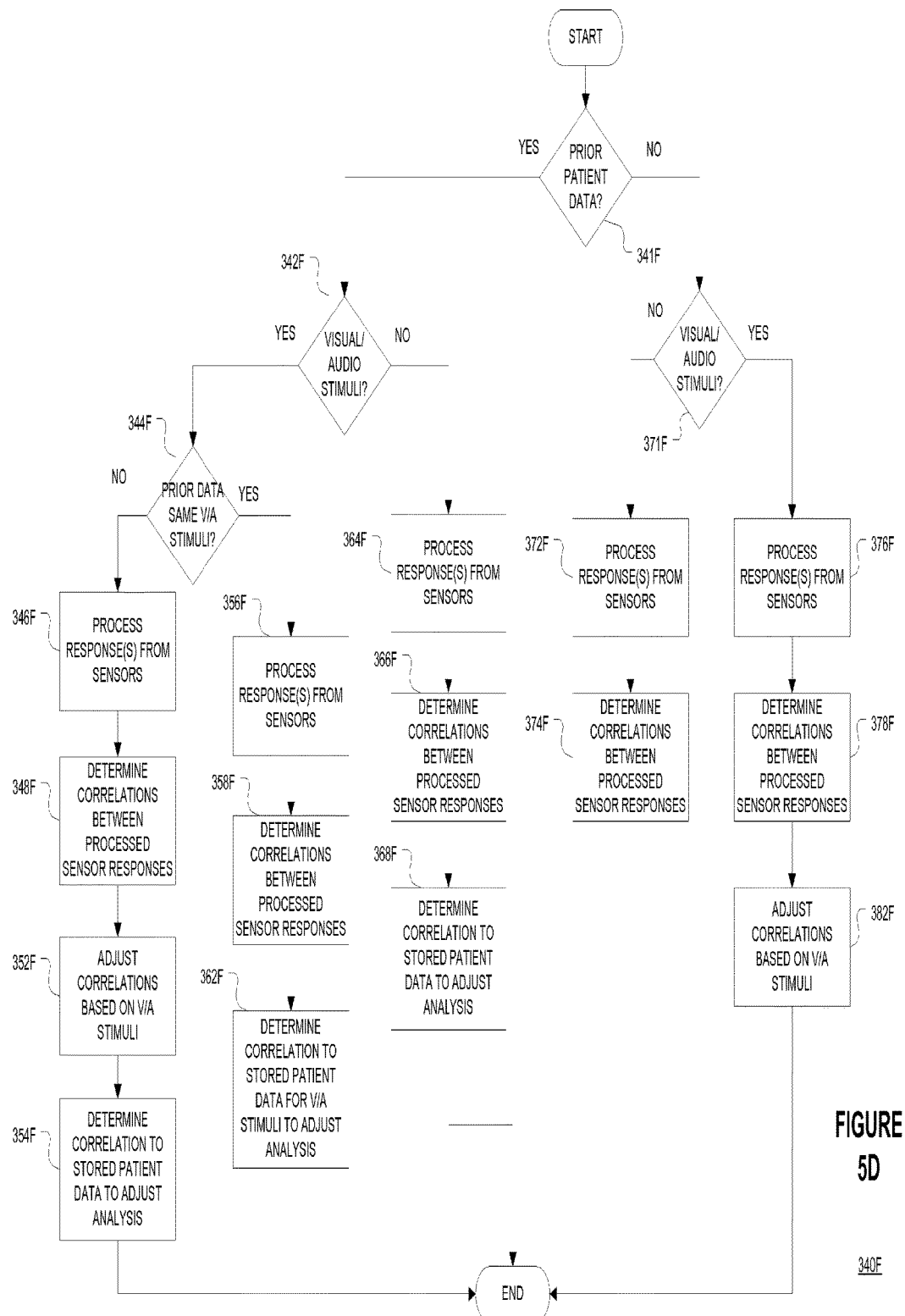

The method 340F shown in FIG. 5D may be employed to perform the activity 346A, 346D, and 346E in FIGS. 5A, 5B, and 5C. As shown in FIG. 5D, the method 340F may determine whether response data (to PGD 32A, transducer 32B, or electrodes 32C) has been recorded for the patient or another patient (to serve as a base for correlation) (activity 341F). When prior patient data exists (activity 341F), method 340F may determine whether V/A data was used in part to generate the responses (from PGD 32A, transducer 32B, or electrodes 32C) to be analyzed (activity 342F). When V/A data is used, the method 340F may further determine whether the prior patient data was recorded in the presence of the same or substantially similar V/A data or stimuli (activity 344F).

When the stored patient data is related to the used V/A stimuli, the method 340F may process the responses from the various sensors (from PGD 32A, transducer 32B, or electrodes 32C) as described above (activity 356F). The method 340F may then determine the correlation between response data received at the various sensors (from PGD 32A, transducer 32B, or electrodes 32C) (activity 358F). The method 340F may then determine the correlation of the resultant correlated received sensor data to the stored patient data for the similar V/A stimuli (activity 362F).

When the stored patient data is not related to the used V/A stimuli (activity 344F), the method 340F may process the responses from the various sensors (from PGD 32A, transducer 32B, or electrodes 32C) as described above (activity 346F). The method 340F may then determine the correlation between response data received at the various sensors (from PGD 32A, transducer 32B, electrodes 32C, or antennas 32E) (activity 348F). The method 340F may then adjust the correlated, received signals based on the V/A stimuli applied (activity 352F). The method 340F may then determine the correlation of the resultant adjusted, correlated received sensor data to the stored patient data (activity 354F).

When the stored patient data is present (activity 341F) but V/A stimuli is not applied (activity 342F), the method 340F may process the responses from the various sensors (from PGD 32A, transducer 32B, electrodes 32C, or antennas 23E) as described above (activity 364F). The method 340F may then determine the correlation between response data received at the various sensors (from PGD 32A, transducer 32B, electrodes 32C, or antennas 32E) (activity 366F). The method 340F may then determine the correlation of the resultant correlated received sensor data to the stored patient data (activity 368F).

When the stored patient data is not present (activity 341F) and V/A stimuli is not applied (activity 371F), the method 340F may process the responses from the various sensors (from PGD 32A, transducer 32B, electrodes 32C, or antennas 32E) as described above (activity 372F). The method 340F may then determine the correlation between response data received at the various sensors (from PGD 32A, transducer 32B, electrodes 32C, or antennas 32E) (activity 374F). When the stored patient data is not present (activity 341F) but V/A stimuli is applied (activity 371F), the method 340F may process the responses from the various sensors (from PGD 32A, transducer 32B, electrodes 32C, or antennas 32E) as described above (activity 376F).

The method 340F may then determine the correlation between response data received at the various sensors (from PGD 32A, transducer 32B, electrodes 32C, antennas 32E) (activity 378F). The method 340F may then adjust the correlations based on the V/A stimuli applied to the patient 22 (activity 382F). In an embodiment the patient data, related patient data, related data, video data, and audio data may be stored in the ROM 406 or the RAM 384. As noted above comparison data for related signals for related devices 32A, 32B, 32C, 32E may also be stored in the ROM 406 and RAM 384. The algorithm 340F may use the comparison data in conjunction with other patient data to determine patient status including injury type, status, and severity. The resultant status may be used to direct therapy.

It is noted that during a traumatic event or stroke a patient's state may change from primarily hemorrhagic tissue to ischemic tissue depending on the therapy applied to the patient. The present invention may be employed to monitor a patient cranial anatomy using multiple signal modalities including electrodes 32C, antennas 32E, transducers 32B, or LDD 33A.

FIG. 6 is a block diagram of an article 380 according to various embodiments. The article 380 shown in FIG. 10 may be used in various embodiments as a part of a system 10A-10E, 100 where the article 380 may be any computing device including an application specific integrated circuit (ASIC), personal data assistant, cellular telephone, laptop computer, or desktop computer. The article 380 may include a central processing unit (CPU) 382, a random access memory (RAM) 384, a read only memory (ROM") 406, a display 388, a user input device 412, a transceiver application specific integrated circuit (ASIC) 416, a digital to analog (D/A) and analog to digital (A/D) convertor 415, a microphone 408, a speaker 402, and an antenna 404. The CPU 382 may include an OS module 414 and an application module 413. The RAM 384 may include a DSP 55 and timers 57.

The ROM 406 may be coupled to the CPU 382 and may store the program instructions to be executed by the CPU 382. The RAM 384 may be coupled to the CPU 382 and may store temporary program data, overhead information, and the queues 398. As noted the ROM 406 and RAM 384 may also store signal correlation data for devices 32A, 32B, 32C, 32E as a function of signal applied to the device. The user input device 412 may comprise an input device such as a keypad, touch pad screen, track ball or other similar input device that allows the user to navigate through menus in order to operate the article 380. The display 388 may be an output device such as a CRT, LCD, LED or other lighting apparatus that enables the user to read, view, or hear user detectable signals.

The microphone 408 and speaker 402 may be incorporated into the device 380. The microphone 408 and speaker 402 may also be separated from the device 380. Received data may be transmitted to the CPU 382 via a bus 396 where the data may include signals for a PGD 32A, PDD 33A, transducer 32B, and electrode 32C. The transceiver ASIC 416 may include an instruction set necessary to communicate data, screens, or signals. The ASIC 416 may be coupled to the antenna 404 to communicate wireless messages, pages, and signal information within the signal. When a message is received by the transceiver ASIC 416, its corresponding data may be transferred to the CPU 382 via the serial bus 396. The data can include wireless protocol, overhead information, and data to be processed by the device 380 in accordance with the methods described herein.

The D/A and A/D convertor 415 may be coupled to one or more a PGD 32A, PDD 33A, transducer 32B, and electrode 32C. Any of the components previously described may be implemented in a number of ways, including embodiments in software. Any of the components previously described may be implemented in a number of ways, including embodiments in software. Thus, a PGD 32A, PDD 33A, transducer 32B, and electrode 32C, antennas 32E, controllers 54, DSP 55, and timers 57 may all be characterized as "modules" herein. The modules may include hardware circuitry, single or multi-processor circuits, memory circuits, software program modules and objects, firmware, and combinations thereof, as desired by the architect of the system 10A-10E, 100 and as appropriate for particular implementations of various embodiments.

The apparatus and systems of various embodiments may be useful in applications other than a sales architecture configuration. They are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, single or multi-processor modules, single or multiple embedded processors, data switches, and application-specific modules, including multilayer, multi-chip modules. Such apparatus and systems may further be included as sub-components within a variety of electronic systems, such as televisions, cellular telephones, personal computers (e.g., laptop computers, desktop computers, handheld computers, tablet computers, etc.), workstations, radios, video players, audio players (e.g., mp3 players), vehicles, medical devices (e.g., heart monitor, blood pressure monitor, etc.) and others. Some embodiments may include a number of methods.

It may be possible to execute the activities described herein in an order other than the order described. Various activities described with respect to the methods identified herein can be executed in repetitive, serial, or parallel fashion.

A software program may be launched from a computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus, the following claims are hereby incorporated into the Detailed Description, with each claim standing on its own as a separate embodiment.

The invention claimed is:

1. A system for evaluating cranial anatomy, including:
   a flexible module configured to engage at least a portion of a patient's cranium;
   a photonic generation module (PGM) at a known location in the flexible module;
   a photonic detection module (PDM) at a known location in the flexible module;
   an acoustic generation module (AGM) at a known location in the flexible module, the AGM configured to generate acoustic energy and receive acoustic energy; and
   a controller, the controller directing the operation of the PGM to generate photonic energy having a first frequency, directing the operation of the AGM to generate acoustic energy having a second frequency, the first frequency different than the second frequency, receiving electrical signals from the PDM representing photonic energy and from the AGM representing acoustic energy; and evaluating a combination of the received signals to determine the status of a section of the at least portion of the patient's cranium.

2. The system for evaluating cranial anatomy of claim 1, further including a memory module, the memory module including signals representing received data for a PDM having various cranium anatomy status and the controller correlating received PDM data with the stored signals to determine a cranium anatomy status.

3. The system for evaluating cranial anatomy of claim 2, the controller applying signals to the plurality of PGM and receiving signals from the corresponding, nearby plurality of PDM and correlating stored PDM data with the received data to determine the physical location of one or more of the plurality of PGM relative to a patient cranial anatomy and correlating the position of the other of the plurality of PGM and the AGM relative to the patient cranial anatomy based on the determined physical location of one or more of the plurality of PGM.

4. The system for evaluating cranial anatomy of claim 3, further including a plurality of antennas at different, known locations in the flexible module to generate low-energy electrical signals and to receive electrical signals, the controller receiving electrical signals from plurality of antennas and evaluating a combination of the received PDM, AGM, and antenna signals to determine the status of a section of the at least portion of the patient's cranium.

5. The system for evaluating cranial anatomy of claim 4, the memory module further including signals representing received data for an antenna at a known location having various cranium anatomy status and the controller correlating received antenna data from a corresponding known location with the stored signals to determine a cranium anatomy status.

6. The system for evaluating cranial anatomy of claim 4, further including a memory module, the memory module including signals representing combined received data for a PDM at a known location, an antenna at a known location, and an AGM at a known location having various cranium anatomy status and the controller correlating received PDM data from the corresponding known location, received antenna data from the corresponding known location, and received AGM data from the corresponding known location with the stored combined signals to determine a cranium anatomy status.

7. The system for evaluating cranial anatomy of claim 6, wherein the antenna generate a low-level electrical signal including microwave frequency content.

8. The system for evaluating cranial anatomy of claim 3, further including a plurality of electrical signal electrodes at different, known locations in the flexible module to receive electrical energy signals generated near the system, the controller receiving electrical signals from plurality of electrical signal electrodes and evaluating a combination of the received PDM, AGM, and electrical signal electrode signals to determine the status of a section of the at least portion of the patient's cranium.

9. The system for evaluating cranial anatomy of claim 8, the memory module further including signals representing received data for an electrical signal electrode at a known location having various cranium anatomy status and the controller correlating received electrical signal electrode data from a corresponding known location with the stored signals to determine a cranium anatomy status.

10. The system for evaluating cranial anatomy of claim 8, further including a memory module, the memory module including signals representing combined received data for a PDM at a known location, an electrical signal electrode at a known location, and an AGM at a known location having various cranium anatomy status and the controller correlating received PDM data from the corresponding known location, received electrical signal electrode data from the corresponding known location, and received AGM data from the corresponding known location with the stored combined signals to determine a cranium anatomy status.

11. The system for evaluating cranial anatomy of claim 2, the memory module further including signals representing received data for a AGM having various cranium anatomy status and the controller correlating received AGM data with the stored signals to determine a cranium anatomy status.

12. The system for evaluating cranial anatomy of claim 1, wherein the system includes a plurality of PGM at different, known locations in the flexible module and a corresponding plurality of PDM at other, different, known locations in the flexible module, a PGM near each of the PDM.

13. The system for evaluating cranial anatomy of claim 12, the flexible module including an anatomical marker to align the plurality of PGM and PDM and AGM relative to the patient's cranial anatomy.

14. The system for evaluating cranial anatomy of claim 12, wherein a PGM produces one of an infra-red and a near infra-red signal.

15. The system for evaluating cranial anatomy of claim 1, further including a memory module, the memory module including signals representing combined received data for a PDM at a known location and an AGM at a known location having various cranium anatomy status and the controller correlating received PDM data from the corresponding known location and received AGM data from the corresponding known location with the stored combined signals to determine a cranium anatomy status.

16. The system for evaluating cranial anatomy of claim 15, wherein the known location is one of a transtemporal window and a transorbital window.

17. The system for evaluating cranial anatomy of claim 16, wherein anatomy status includes one of detecting ischemic tissue and detecting hemorrhagic tissue at or near the known location.

18. The system for evaluating cranial anatomy of claim 1, further including a memory module, the memory module including signals representing received data for a PDM at a known location having various cranium anatomy status and the controller correlating received PDM data from the corresponding known location with the stored signals to determine a cranium anatomy status.

19. The system for evaluating cranial anatomy of claim 18, the memory module further including signals representing received data for a AGM at a known location having various cranium anatomy status and the controller correlating received AGM data from the corresponding known location with the stored signals to determine a cranium anatomy status.

20. The system for evaluating cranial anatomy of claim 1, wherein the system is portable and includes an electrical energy module to provide power to the modules.

* * * * *